US00PP30167P3

(12) United States Plant Patent
Danziger

(10) Patent No.: US PP30,167 P3
(45) Date of Patent: Jan. 29, 2019

(54) ***CALIBRACHOA* PLANT NAMED 'DCALCOFUCH'**

(50) Latin Name: ***Calibrachoa* hybrid**
Varietal Denomination: DCALCOFUCH

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/731,163

(22) Filed: Apr. 26, 2017

(65) Prior Publication Data

US 2018/0317361 P1 Nov. 1, 2018

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./263.1, 413
See application file for complete search history.

(56) References Cited

PUBLICATIONS

Malmborg's Greenhouse Spring 2017. https://issuu.com/erin2350/docs/2017_catalog_online. Accessed Jun. 8, 2018. 4 pages.*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Calibrachoa* cultivar named 'DCALCOFUCH' is disclosed, characterized by a mounded growth habit and day length neutral flowering. The plants flower early and abundantly. The flower has a vibrant fuchsia color with a bright yellow throat. The new variety is a *Calibrachoa*, normally produced as an outdoor garden or container plant.

2 Drawing Sheets

Figure 1:
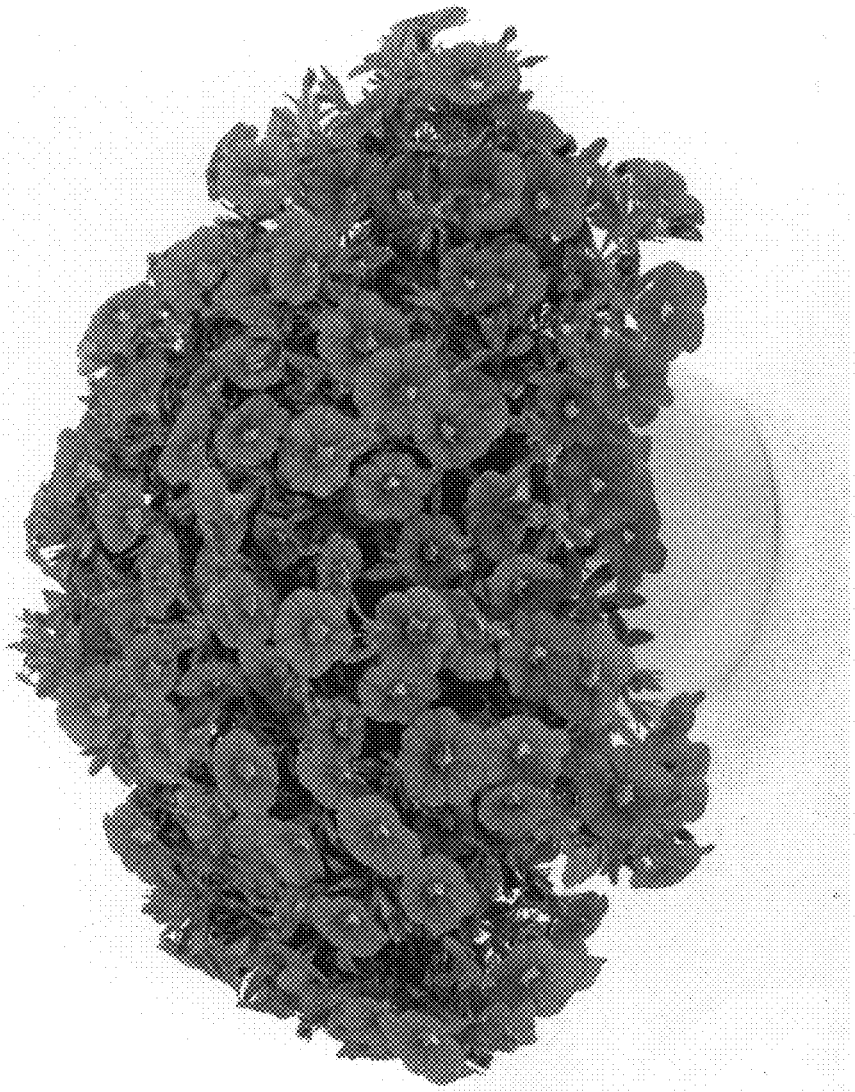

Latin name of the genus and species: *Calibrachoa* hybrid.
Variety denomination: 'DCALCOFUCH'.

BACKGROUND OF THE INVENTION

The new *Calibrachoa hybrida* cultivar is a product of a planned breeding program conducted by the inventor, Gavriel Danziger in Moshav Mishmar Hashiva, Israel. The objective of the breeding program was to produce new *Calibrachoa* varieties. The cross resulting in this new variety was made during April of 2014.

The seed parent is the unpatented, propriety variety referred to as *Calibrachoa* 'cv. 12-2940'. The pollen parent is the unpatented, propriety variety referred to as *Calibrachoa* 'cv. 13-3598'. The new variety was discovered in November of 2014 by the inventor in a group of seedlings resulting from the 2014 crossing, in a greenhouse in Moshav Mishmar Hashiva, Israel.

Asexual reproduction of the new cultivar 'DCALCOFUCH' was first performed by terminal vegetative cuttings at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DCALCOFUCH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALCOFUCH' These characteristics in combination distinguish 'DCALCOFUCH' as a new and distinct *Calibrachoa* cultivar:

1. Mounded habit.
2. Early flowering.
3. Day length neutral flowering.
4. Abundant flowering.
5. Vibrant flower color, fuchsia petals and a bright yellow tube.

PARENT COMPARISON

Plants of the new cultivar 'DCALCOFUCH' are similar to plants of the seed parent, *Calibrachoa* 'cv. 12-2940' most horticultural characteristics, however, plants of the new cultivar 'DCALCOFUCH' differ in the following;

1. The seed parent has a trailing plant habit, the new variety is mounded.
2. The seed parent flower color is dark red, flower color of the new variety is fuchsia with a yellow center.
3. The new variety has a shorter internode length.

Plants of the new cultivar 'DCALCOFUCH' are similar to plants of the pollen parent, *Calibrachoa* 'cv. 13-3598' most horticultural characteristics however, plants of the new cultivar 'DCALCOFUCH' differ in the following;

1. The pollen parent has a trailing growth habit, the new variety is mounded.

2. The new variety has a bright yellow throat not seen in the pollen parent.
3. The new variety has a shorter internode length.
4. The pollen parent has smaller flowers than the new variety.

COMMERCIAL COMPARISON

Plants of the new cultivar 'DCALCOFUCH' can be compared to the unpatented commercial variety *Calibrachoa* 'Danoa30'. These varieties are similar in most horticultural characteristics; however, 'DCALCOFUCH' differs in the following:

1. 'DCALCOFUCH' flowers earlier than this comparator.
2. 'DCALCOFUCH' color is dark fuchsia, the comparator flower color is light pink.
3. 'DCALCOFUCH' has a mounded habit, 'Danoa30' has semi-trailing habit.

Plants of the new cultivar 'DCALCOFUCH' can also be compared to the unpatented commercial variety *Calibrachoa* 'DCALNOARAS'. These varieties are similar in most horticultural characteristics; however, 'DCALCOFUCH' differs in the following:

1. 'DCALCOFUCH' is less vigorous in growth than this comparator.
2. 'DCALCOFUCH' color is a different shade of bright pink/fuchsia.
3. 'DCALCOFUCH' habit is mounded, this comparator habit is semi trailing.

BRIEF DESCRIPTION OF THE PHOTOGRAPHS

The accompanying photograph in FIG. 1 illustrates in full color a typical plant of 'DCALCOFUCH' grown in a greenhouse, in Moshav Mishmar Hashiva, Israel.

Figure 2:
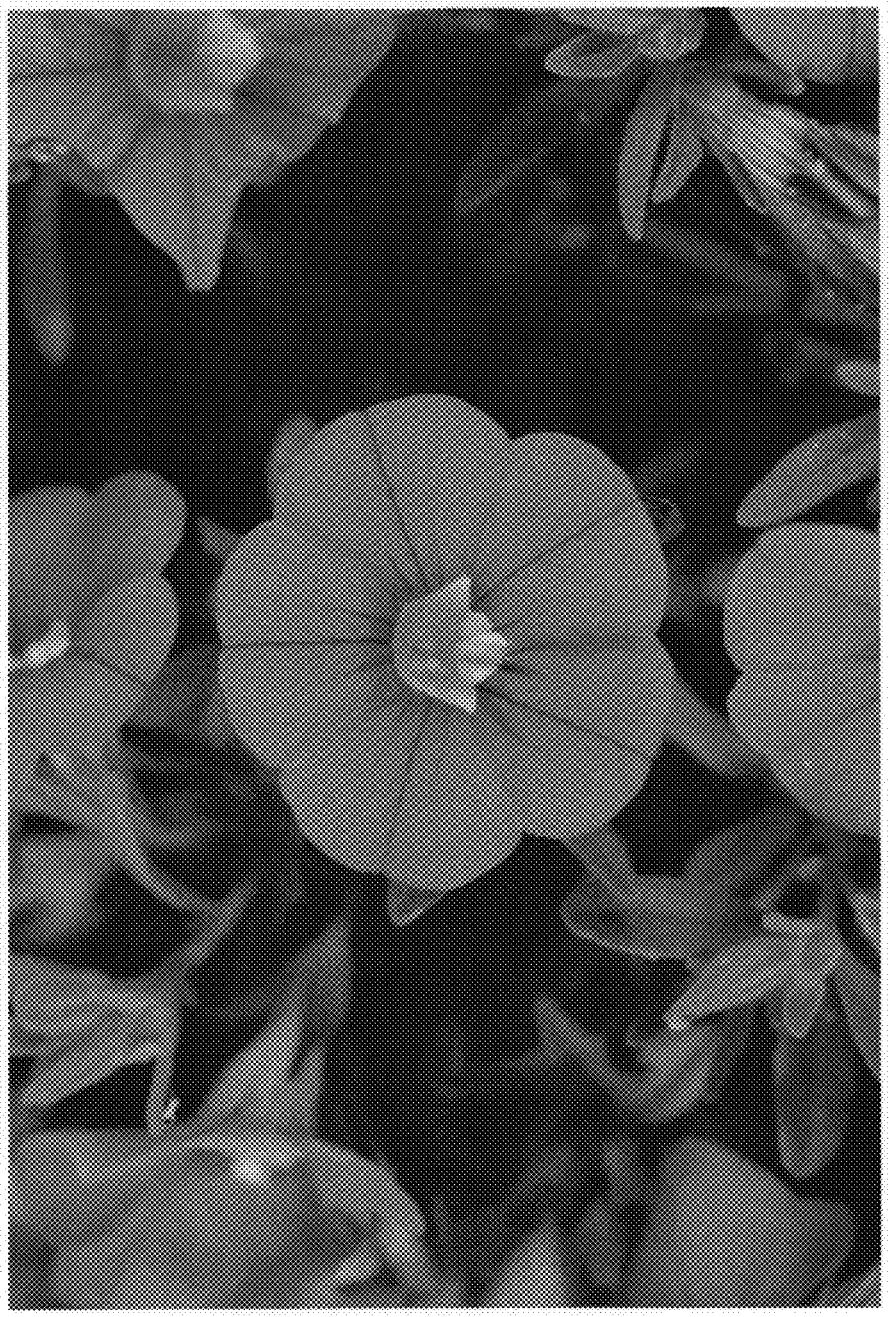

FIG. 2 illustrates in full color a typical mature flower of 'DCALCOFUCH'. Age of the plant photographed is approximately 60 days from a rooted cutting in a 13 cm pot. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALCOFUCH' plants grown in greenhouse in Moshav Mishmar Hashiva, Israel, under natural lighting. Measurements were taken during April of 2016. The plants were approximately 60 days from a rooted cutting in a 13 cm pot. The growing temperature ranged from 15° C. to 28° C. during the days, 15° C. to 20° C. during the nights. Measurements and numerical values represent averages of typical plant types.

Botanical classification: *Calibrachoa* hybrid 'DCALCOFUCH'.

PROPAGATION

Time to initiate roots: 10-15 days at approximately 20° C.
Root description: Fibrous. Colored tan and white, not accurately measured with R.H.S. chart.

PLANT

Growth habit: Mounded.
Pot size, of plant described: 13 cm.
Height: To top of flowers: 14 cm.
Plant spread: 30 to 40 cm.
Growth rate: Medium.
Branching characteristics:
Length of primary lateral branches: 13 to 15 cm.
Diameter of lateral branches: 0.2 to 0.3 cm.
Quantity of primary lateral branches: 6 to 7.
Characteristics of primary lateral branches:
*Form*.—Cylindrical to Laterally compressed.
*Diameter*.—0.2 to 0.3 cm.
*Color*.—Yellow-Green 146C.
*Texture*.—Hispid.
*Strength*.—Good, flexible.
Internode length: 0.5 to 1 cm.

FOLIAGE

Leaf:
Leaf:
*Arrangement*.—Alternate.
*Quantity*.—Approximately 50 per branch.
*Average length*.—3.2 cm.
*Average width*.—1.2 cm.
*Shape of blade*.—Elliptic.
*Apex*.—Rounded.
*Base*.—Acuminate.
*Margin*.—Entire.
*Texture of top surface*.—Glabrous.
*Pubescence*.—Scabrous.
*Aspect*.—90 degrees.
*Color*.—Young foliage upper side: Near RHS Green 137B. Young foliage under side: Near RHS Green 138B. Mature foliage upper side: Near RHS Green 137A. Mature foliage under side: Near RHS Green 138B.
*Venation*.—Type: Pinnate. Venation color upper side: Near RHS Green 137A. Venation color under side: Near RHS Green 138B.
*Petiole*.—Length: 0.3 to 0.4 cm. Diameter: 0.1-0.15 cm. Color: Near RHS Green 137B. Texture: Glabrous.

FLOWER

Natural flowering season: All seasons.
Days to flowering from rooted cutting: 20 to 30 days.
Inflorescence and flower type and habit: Individual salverform flowers, outwardly facing.
Rate of flower opening: 2 to 3 days from bud to fully opened flower.
Flower longevity on plant: 4 to 7 days.
Approximate quantity of flowers per plant: About 50.
Persistent or self-cleaning: Self-cleaning.
Bud:
*Shape*.—Ovoid.
*Length*.—0.4 cm.

*Diameter.*—0.3 cm.
*Color.*—Near RHS Yellow-Green 145B.

Flower size:
*Diameter.*—4.3 cm.
*Length.*—4.3 cm.
*Flower tube diameter at distal end.*—1 cm.
*Flower tube diameter at proximal end.*—0.3 cm.

Petals:
*Length from throat.*—1.6 to 1.8 cm.
*Width.*—2 cm.
*Quantity.*—5.
*Texture.*—Glabrous.
*Apex.*—Emarginated.
*Margin.*—Entire.

Color:
*When opening.*—Upper surface: Near RHS Red-Purple N74A RHS. Lower surface: Near RHS Red-Purple N74C RHS.
*Fully opened.*—Upper surface: Near RHS Red-Purple N74A with Red-Purple 61A veins. Lower surface: Near RHS Red-Purple N74C with 61A veins. Flower throat (inside): Near Yellow 8B. Flower throat, vein: Near Violet 85C. Flower tube (outside): Near Yellow 8D. Flower tube, vein: Near Violet 83A. Petal color, fading to: Near RHS Red-Purple N74B.

Calyx/sepals:
*Quantity per flower.*—5.
*Shape.*—Lance-Shaped (lanceolate).
*Length.*—1.5 cm.
*Width.*—0.5 cm.
*Apex.*—Rounded.
*Base.*—Cuneate.
*Margin.*—Entire.
*Texture.*—Glabrous.
*Color.*—Upper Surface: Yellow-Green 146A. Lower Surface: Yellow-Green 146B.

Peduncle: Not Relevant.

Pedicel:
*Length.*—2 cm.
*Diameter.*—0.1 cm.
*Color.*—Yellow-Green 147C.
*Orientation.*—45 degrees.

Fragrance: None.

REPRODUCTIVE ORGANS

Stamens:
*Number.*—5.
*Filament length.*—0.5 to 0.9 cm.

Anthers:
*Length.*—0.1 cm.
*Shape.*—Globose.
*Color.*—Near Yellow 9C.
*Pollen.*—Color: Near Yellow 9D. Quantity: Moderate.

Pistil:
*Number.*—1.
*Length.*—1 cm.
*Style.*—Length: 0.6 cm. Color: Yellow-Green 147D.
*Stigma.*—Shape: Oblate. Color: Yellow-Green 147B. Ovary Color: Yellow-Green 147D.

OTHER CHARACTERISTICS

Seeds and fruits: About 30 Brown, rounded seeds of about 0.5 mm diameter, per one brown, conical capsule. Capsule light brown, seeds dark brown, neither accurately measured with R.H.S. chart.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium.*

Temperature tolerance: 5° C. to 30° C.

Drought tolerance: No tolerance for drought.

What is claimed is:

1. A new and distinct cultivar of *Calibrachoa* plant named 'DCALCOFUCH' as herein illustrated and described.

* * * * *